United States Patent [19]
Pap et al.

[11] Patent Number: 5,389,662
[45] Date of Patent: Feb. 14, 1995

[54] COMBINED COMPOSITIONS

[75] Inventors: László Pap, Budapest; István Székely, Dunakeszi; Lajos Nagy, Szentendre; András Szegó, Budapest; Andrea Tóth, Solymár; Éva Somfai, Budapest; Csaba Szántay, Budapest; Lajos Novák, Budapest; László Poppe, Budapest, all of Hungary

[73] Assignee: Chinoin Gyogyszer Es Vegyeszeti Termekek Gyar Rt., Budapest, Hungary

[21] Appl. No.: 687,938
[22] PCT Filed: Jul. 30, 1990
[86] PCT No.: PCT/HU90/00055
 § 371 Date: May 31, 1991
 § 102(e) Date: May 31, 1991
[87] PCT Pub. No.: WO91/01640
 PCT Pub. Date: Feb. 21, 1991

[30] Foreign Application Priority Data

Jul. 31, 1989 [HU] Hungary ............... 3913/89

[51] Int. Cl.6 .............................. A01N 43/28
[52] U.S. Cl. ......................... 514/383; 514/521
[58] Field of Search ................. 514/383, 521

[56] References Cited

U.S. PATENT DOCUMENTS 5,013,746 5/1991 Van Gestel ............... 514/383

FOREIGN PATENT DOCUMENTS

| 0050738 | 5/1982 | European Pat. Off. | 514/383 |
| 0148526 | 7/1985 | European Pat. Off. | |
| 8604215 | 7/1986 | WIPO | 514/521 |
| 8604216 | 7/1986 | WIPO | 514/521 |

OTHER PUBLICATIONS

Journal of Chemical Ecology, vol. 13, No. 3, pp. 423–436 (1987).
Pestic. Sci. 1984, vol. 15, pp. 133–155 Mercer.
Pestic. Sci. 1987, vol. 21, pp. 289–306 Bosche et al.
M. B. Green and D. A. Spilker, ACS Symposium Series, pp. 25–51 (1986).
The Biochemical Mode of Action, eds. J. R. Corbett, K. Wright and A. C. Baillie, pp. 256–268 (1984).
Plant Pathogenic Fungi (in Hungarian) L. Vajna, pp. 118–119 (1987).

Primary Examiner—Allen J. Robinson
Assistant Examiner—Brian M. Burn
Attorney, Agent, or Firm—Herbert Dubno; Jonathan Myers

[57] ABSTRACT

The invention relates to novel combined compositions for combatting plant, animal and sanitarian as well as forestry, horticultural and warehouse pests. These compositions contain a pyrethroid-type insecticide as an insecticidally active ingredient and at least one fungicide inhibiting the ergosterol biosynthesis as activity-strengthening agent as well as optionally piperonyl-butoxide and other additives.

The advantages of the compositions according to the invention consist therein that the activity-strengthening substances used are fungicidal agents widely used and have an advantageous toxicology. The activity-strengthening agent exerts a synergistic effect together with the pyrethroid-type insecticide.

The combinations according to the invention bear an outstanding importance in the protection of stored crops.

2 Claims, No Drawings

COMBINED COMPOSITIONS

CROSS REFERENCE TO RELATED APPLICATION

This application is a national phase application of PCT/HU90/00055 filed 30 Jul. 1990 and based upon a Hungarian national application 3913/89 under the International Convention.

This invention relates to novel combined compositions for combatting plant, animal and sanitarian as well as forestry, horticultural and warehouse pests, which contain a pyrethroid-type insecticide as an insecticidally active ingredient and at least one fungicide inhibiting the ergosterol biosynthesis, optionally piperonylbutoxide as an activity-strengthening agent and other additives.

BACKGROUND OF THE INVENTION

In recent years, the most recently developed class of active agents, i.e. pyrethroids have continuously increased in importance. However, some undesired side effects were also observed during their intense utilization. Due to their contact mode of action, they kill not only the arthropods damaging cultivated plants but frequently the useful entomophages, consuming the arthropods. By decreasing the number of the natural enemies, the rate of repeated multiplication of the pests is enhanced, which may influence the specific use of agents, too. In extreme cases, the excessive and unadvised use of the agents may lead to such a decrease in the number of useful entomophages that, due to the lack of regulation, the agriculturally indifferent arthropods, playing an unimportant role in fauna, may become so-called "man-made" pests (A. W. A. Brown: "Ecology of Pesticides", Wiley-Sons, 1978).

Another problem is connected with the strongly specific action mechanism of pyrethroids causing a higher risk of the development of resistance than is the case with the traditional agents.

DESCRIPTION OF THE INVENTION

The present invention is based on the surprising discovery that fungicides inhibiting biosynthesis of ergosterol, which are used both as medicines and plant-protective agents, are capable of extraordinarily increasing the insecticidal efficiency of pyrethroids.

Ergosterol is an indispensable constituent of the fungal cell membrane. When the biosynthesis of ergosterol is blocked by any inhibitor, the fungus will be destroyed due to the lack of ergosterol, possibly an effect of the precursors accumulated.

Each of the compounds inhibiting the biosynthesis of ergosterol, known to the present, acts on the intermediate reactions of enzymatic processes playing a role in the transformation of lanosterol to ergosterol ("The Biochemical Mode of Action", eds. J. R. Corbett, K. Wright and A. C. Baillie, Academic Press, London, pages 256–268, 1984). These processes catalyzed by the cytochrome P-450 system of fungi are characterized by a high degree of substrate- and species-specifity [Pestic. Sci. 15, 133 (1984)]. On the one hand, this led to the description of selectively utilizable pathogen-specific inhibitors and on the other hand, this led to the recognition that the effect of the individual inhibitors on various species cannot be predicted "Fungicide Chemistry: Advances and Practical Applications", eds. M. B. Green and D. A. Spilker, ACS Symposium Series, pages 25 to 51, 1986). The diversity appearing in the species-specificity of inhibitors is characteristic of the whole living world [Biochimie 69, 743 (1987)].

It is known that the azole-type fungicides inhibiting the ergosterol biosynthesis (azaconazole, penconazole, propiconazole, imazalil, myconazole, clotrimazole, bifenazole, ketoconazole, itraconazole, fluconazole) inhibit only the functioning of the fungal microsomal cytochrome P-450 system and practically have no effect on that of plants of higher order and on that of mammals [Pestic. Sci. 21, 289 (1987)]. The effect of inhibitors of the ergosterol biosynthesis is so highly specific that they have no influence on the activity of microsomal oxidases containing another cytochrome P-450 component ["Plant-Pathogenic Fungi" (in Hungarian), ed. L. Vajna, Mezögazdasági Könyvkiadó, page 119, Budapest 1987].

Characteristically, in opposition to diterpenes and monoterpenes, triterpenes (stigmasterol, sitosterol, squalene or ergosterol) are not metabolized or are metabolized only after induction to a very small extent and nonspecifically by a microsomal oxidase preparation arising from the larvae of a moth (*Spodoptera frugiperda*) [J. Chem. Ecol. 13, 423 (1987)].

The facts discussed above indicate that inhibitors of the enzymes participating of the biosynthesis of ergosterol have no effect on the microsomal enzymes of insects. No other mechanism of action is known from the literature, through which these inhibitors might exert an influence on the efficiency of pyrethroid-type insecticides used against insects.

It has been recognized during our investigations that the insecticidal activity of pyrethroids was significantly enhanced by the addition of several fungicides inhibiting the biosynthesis of ergosterol.

The combined compositions according to the invention can be used in the common manner, e.g. by dipping, sprinkling, spraying, spreading, fuming, dusting, bathing, impregnating the packaging material and the like. The amount applied depends on the good and in general amounts to 2–25 g/hectare (hereinafter abbreviated: g/ha) or 0.10–2 g/ha of active ingredient combination, respectively calculated for 100 g of seed grains or propagating material. The combined compositions according to the invention can be used together with herbicides, insecticides, growth-regulating agents or fertilizers and disinfectants (for extending the possibilities of utilization and protection).

It may be preferable to add an activating agent or a further synergistic agent, e.g. piperonylbutoxide to the combination. Thereby, the efficiency of the active ingredient will be increased without enhancing the toxicity on warm-blooded animals.

The combination according to the invention can be formulated to the usual compositions, such as solutions, emulsion concentrates, suspensions, powders, sprayable powders, dusting powders, pastes, granulates, aerosols, dressing composition and the like. The combination of the active ingredients is dissolved or dispersed or ground in the usual diluting agents, e.g. in liquid solvents, in gases liquefied under pressure and/or with solid carriers, optionally in the presence of a surface active additive or they are formulated in an other known way.

Suitable liquid solvents are e.g.: mineral oil fractions with a medium or high boiling point such as kerosine or gas oil, vegetable oils or oils of animal origin; aliphatic, cyclic and aromatic hydrocarbons such as toluene, xylene, alkylated naphthalenes, cyclohexane, paraffin or their derivatives such as lower alcohols, glycols, esters, ketones and halogenated hydrocarbons, e.g. butanol, ethylene glycol, methyl ethyl keton, cyclohexanone, chloroform, chlroobenzene; or a polar solvent, e.g. dimethylformamide, dimethyl sulfoxide or N-methylpyrrolidone. Suitable liquefied gases are e.g. the propellant gases of common aerosols, e.g. halogenated hydrocarbons such as freon as well as butane, propane, nitrogen or carbon dioxide.

Suitable solid carriers may be e.g. mineral grists of native origin, stone grists such as kaolin, clays, talc, chalk, quartz, attapulgite, montmorillonite, diatomaceous earth, siliceous earth or artificial mineral grists, e.g. highly dispersed silicic acid, aluminum oxide and silicates. As carriers for granulates, crushed native minerals, e.g. calcite, marble, chalk, dolomite, synthetic granulates prepared from an organic or inorganic grist as well as granulates prepared form an organic material such as sawdust, maize stalk and stump, tobacco stalk, poppy wastes or bran of furfural may be employed.

Preferable surface active additives are emulsifying and/or dispersing agents and/or antifoaming agents, e.g.: alkali metal, alkaline earth metal and ammonium salts of ligninsulfonic, naphthalenesulfonic and phenolsulfonic acids; alkylaryl sulfonates, alkyl sulfates, alkyl sulfonates; alkali and alkaline earth metal salts of dibutylnaphthalenesulfonic acid; lauryl ether sulfate, fatty alcohol sulfates; alkali metal and alkaline earth metal salts of fatty acids; salts of sulfated hexadecanols, heptadecanols and octadecanols; salts of sulfated fatty alcohol glycol ethers; condensation products from sulfonated naphthalene and naphthalene derivatives with formaldehyde; polyoxyethylene octylphenyl ether; ethoxylated isooctylphenol, octylphenol and nonylphenol; alkylphenyl polyglycol ether, tributylphenyl polyglycol ether; alkylaryl polyether alcohol; isotridecyl alcohol; condensation products of fatty alcohols with ethylene oxide; ethoxylated castor oil; polyoxyethylene alkyl ether; ethoxylated polyoxypropylene; lauryl alcohol polyglycol ether acetal; sorbitol esters; sulfit wastes; as well as methylcellulose.

According to the present invention, various wettable powders and dispersifiable granulates containing the active ingredients in a total amount of 1 to 95% by weight may be prepared. It is suitable to add an anionic and/or nonionic surface active agent in an amount of 0.1 to 10% by weight as auxiliary material. For this purpose e.g. the alkali metal salts of alkyl or aryl sulfonic acids, alkali, metal salts of the condensation products of alkylarylsulfonic acids with formaldehyde, alkylaryl polyglycol ethers, sulfated higher alcohols, polyethylene oxides, sulfated fatty alcohols, fatty acid polyglycol ethers and other commercially available surface active agents may be employed. Other additives are: an anti-adhesive (in an amount of 0.5 to 10% by weight), adhesive (in an amount of 1 to 2% by weight) and filling or carrier material (in an amount of 10 to 60% by weight).

According to the present invention, an emulsion concentrate may also be prepared. This composition preferably contains the active ingredients in a total amount of 5 to 50% by weight together with 50 to 95% by weight of an additive providing a stable emulsion when the emulsion concentrate is emulsified with water or in the presence of water.

It is suitable to use as auxiliary material 0.1 to 2% by weight of a tenside and/or 0.1 to 5% by weight of a stabilizing agent and an amount of an organic solvent supplementing the mixture up to 100% by weight. It is preferable to employ a mixture of anionic and nonionic tensides as tenside. Preferred anionic tensides are e.g. the following products:

Calcium salts of alkylaryl sulfonic acids, e.g. calcium (sodium, potassium) dodecyl benzenesulfonate such as:
SULFARIL-50 (United Chemical Works, Hungary)
MARLON AFR (Hüls)

Mono- and diesters of phosphoric acid, e.g. mono- or di(oxyethylaryl) ester of orthophosphoric acid such as: "Gafac RM 520" (GAF)

Mono- or di(oxyethylalkyl) ester of orthophosphoric acid such as "SURFACTANT QS-5" (Rohm and Haas). Preferred nonionic tensides are e.g.:

Nonyl and tributylphenol polyethylene glycol ethers such as:
ANTAROX, IGEPAL (GAF)
ARKOPAL, EMULSOGEN (Hoechst)
AVOLAN, EMULSIFIER (Bayer)
DOWTAX (DOW)
CATAREX (Shell)
RENEX Atlas)

Adducts of fatty alcohols with ethylene oxide such as:
BRIJ (Atlas)
DISPERSOL A (ICI)
GENAPOL S-XO (Hoechst)

Ethoxylated amines such as:
G-3525 (ethoxylated alkylamine) (Atlas)
G-3684 (ethoxylated alkylamine) (Atlas)
GENAMIN S (ethoxylated stearylamine) (Hoechst)
NEOVADINE AL (ethoxylated alkylamine) (Ciba-Geigy)

Esters of fatty acids with polyethylene glycol such as:
MYRJ 49 (Atlas)
MYRJ 51 (Atlas)
MYRJ 52 (Atlas)
MYRJ 53 (Atlas)
SIOTOL AF (ICI)
NINISOL 110 (Ciba-Geigy)

Prepared mixtures of tensides, e.g. the Geronol (Rhone-Poulenc) products may also be used: from these e.g. FF/4 is a mixture of ethoxylated alkylphenols and calcium dodecylbenzenesulfonate in isobutanol; and the product M S is a mixture of calcium dodecylbenzenesulfonate, ethoxylated amines and ethoxylated fatty acids in isobutanol.

Useful solvents for the above purpose are aromatic solvent mixtures as well as xylene, cyclohexanol, butanol methyl ethyl ketone, isopropanol and the like.

The active ingredient combination according to the invention may also be applied in the form of an aerosol spray. Various liquefied gases such as freons or mixtures of propane and butane may be used as propellant.

Suitable solvents which are used in an amount supplementing the mixture up to 100% by weight are as follows:

Aromatic solvents, e.g. xylene or toluene;
aliphatic or cycloaliphatic alcohols, e.g. butanol, isopropanol, cyclohexanol;
aliphatic ketones, e.g. acetone, methyl ethyl ketone, diethyl ketone;
oils of plant, animal or mineral origin, e.g. olive oil, sunflower oil, rape-seed oil, petroleum, kreolin; or mixtures of aliphatic hydrocarbons, e.g. kerosine; and water.

A preferred suspension concentrate according to the invention contains the active ingredients in a total amount of 0.1 to 30% by weight, optionally together with 2 to 30% by weight of piperonylbutoxide and 99.9 to 40% by weight of additives such as 1 to 10% by weight of a surface active agent, 5 to 10% by weight of an anti-freezing agent, 50 to 90% by weight of a diluting agent or a carrier, 0.2 to 0.3% by weight of a viscosity-increasing agent and 0.1 to 0.3% by weight of an anti-foaming agent.

The granulate contains the active ingredients in a total amount of 1 to 20% by weight as well as optionally 2 to 30% by weight of piperonylbutoxide together with 80 to 99% by weight of an additives such as 5 to 15% by weight of a diluent and 70 to 80% by weight of a solid carrier.

The combined composition according to the present invention may contain 2,6-di(tert-butyl)-4-methyl-phenol, 2,2-dimethyl-4-sulfonylmethyl-1,2-dihydroquinoline, hydroquinone, hydroquinone monomethyl ether, benzophenone, 2,2,4-trimethyl-1,2-dihydroquinoline and/or a phenyl salicylate derivative as antioxidant in an amount of 0.01 to 1% by weight calculated for the active ingredient.

The advantages of the combinations according to the invention can be summarized without any demand on completeness as follows:

1. The material costs of treatments are reduced by decrease in the amount of active ingredient required to achieve the desired effectiveness.
2. The load of the environment by nature-alien substances is decreased.
3. The activity-strengthening substances used in the combinations according to the present invention in themselves are fungicidal agents widely and successfully used, which maintain and in certain cases even increase their fungicidal effectiveness in their mixtures according to the claims. This provides their reasonable incorporation into technologies of plant protection and gives a possibility for simultaneous protection with enhanced efficiency against pests and pathogens.
4. The activity-strenghening substances used in the combinations according to the invention are commercially available agents which are regarded as toxicologically advantageous and the use of which bears only a low risk concerning the safety.
5. The activity-strengthening substances used in the combinations according to the invention increase not only the contact insecticidal effectiveness but, after resorption into the plants, they enhance also the effectiveness against sucking and biting pests whereby the spectrum of activity of pyrethroids is broadened.
6. The combinations according to the invention are of an outstanding importance in the protection of stored crops, where the approved values of residues are critically judged in the cases of both the crops serving as fodders or human alimentation.
7. The combined treatments exert an excellent effect against the phenotypically resistant pests and significantly slow down the rate of the development of resistance.
8. Due to the systemic character of the activity-strengthening substances used in the combinations according to the invention, the toxicity of pyrethroids exerted on the useful entomophages is significantly reduced by the decrease in the effective dose.

In our description the so-called common or ISO names were used for the denomination of the compounds. The chemical nomenclature of these names is known (IUPAC; C.A.) e.g. from the 8th Edition of "The Pesticide Manual" or from "Agricultural Chemicals" compiled by W. T. Thompson, or from other known handbooks. Exceptions are:

Chinmix, which is an isomer mixture of defined ratio of cypermethrin, wherein cis:trans=4:6 and (1R)-cis-(S):(1S)-cis-(R)=1:1 and (1R)-trans-(S):(1S)-trans-(R)=1:1; and Transmix, which is an isomer mixture of defined ratio of cypermethrin, wherein cis:trans=0:1 and (1R)-trans-(S):(1S)-trans-(R)=1:1.

SPECIFIC EXAMPLES

The effectiveness of combinations according to the present invention will hereinafter be illustrated in some biological examples without any demand on completeness and without any restriction of the appended claims.

Biological Examples

Example 1

The insecticidal effectiveness of combinations according to the present invention is hereinafter illustrated on the domestic fly (*Musca domestica*). Female flies of 2 to 4 days age (obtained from WHO) with normal sensitivity were used in these examinations. The active agents were dissolved in 2-ethoxy-ethanol and applied in drops of 0.2 µl onto the dorsal cuticle of the thorax of flies mildly narcotized by carbon dioxide.

20 Flies for each dose and 10 flies for each repetition were used. The examinations were carried out in 2 to 3 repetitions. After the treatments, the flies were placed in plastic dishes covered with sieve cloth and supplied with sugar as food.

After 24 hours the dead flies were counted and the mortality ratio was expressed as percentage. The results are summarized in Table 1.

TABLE 1

| Pyrethroid active ingredient | Dose (ng/fly) | Mortality (%) during 24 hours Alone | After pretreatment* | Increase in effect (%) |
|---|---|---|---|---|
| Permethrin | 20 | 37.5 | 100 | 62.5 |
| Tetramethrin | 300 | 45 | 100 | 55 |
| Fenvalerate | 40 | 57.5 | 100 | 42.5 |
| Cypermethrin | 2.5 | 12.5 | 70 | 57.5 |
|  | 5 | 30 | 90 | 60 |
|  | 10 | 50 | 100 | 50 |
| Deltamethrin | 1 | 40 | 100 | 60 |
| Chinmix | 1 | 5 | 45 | 40 |
|  | 2 | 22.5 | 70 | 47.5 |
|  | 4 | 52.5 | 100 | 47.5 |
| Transmix | 5 | 32.5 | 95 | 62.5 |
|  | 10 | 62.5 | 100 | 37.5 |

*The pretreatment was carried out with 500 ng/0.5 /ul/female fly of propiconazole 1 hour before the treatment. The pretreatments did not induce any symptom or death.

It is unambiguously shown by the Table that the otherwise ineffective pretreatments with 500 ng of oropiconazole significantly increased the effectiveness of all pyrethroids investigated by about 40 to 60%.

Example 2

The synergistic effect of several structurally different inhibitors of the ergosterol biosynthesis is shown in Table 2. The investigation was carried out as described in Example 1.

TABLE 2

| Pretreatment* Dose (ng/fly) | Treatment | Mortality (%) during 24 hours Alone | After pretreatment | Increase in effect (%) |
|---|---|---|---|---|
| Propiconazole | Bioresmethrin | | | |
| 500 ng | 40 ng | 65.0 | 100 | 35 |
| Etaconazole | Tetramethrin | | | |
| 500 ng | 200 ng | 37.5 | 82.5 | 45 |
| 1000 ng | 200 ng | 37.5 | 100 | 62.5 |
| Fenarimol | Tetramethrin | | | |
| 500 ng | 200 ng | 37.5 | 100 | 62.5 |
| Fenarimol | Chinmix | | | |
| 200 ng | 4 ng | 50.0 | 92.5 | 42.5 |
| Bitertanol | Chinmix | | | |
| 500 ng | 4 ng | 50.0 | 85.0 | 35.0 |
| Dichlobutrazole | Chinmix | | | |
| 500 ng | 4 ng | 50.0 | 92.5 | 42.5 |
| 200 ng | 4 ng | 50 | 90 | 40 |
| Flutriafol | Chinmix | | | |
| 500 ng | 4 ng | 50 | 100 | 50 |
| 100 ng | 4 ng | 50 | 100 | 50 |
| 50 ng | 4 ng | 50 | 92.5 | 42.5 |
| 50 ng | 2 ng | 17.5 | 67.5 | 50 |
| Prochloraz | Cypermethrin | | | |
| 500 ng | 10 ng | 55 | 92.5 | 37.5 |
| 200 ng | 10 ng | 55 | 90.0 | 35.0 |

*The pretreatments did not induce any symptom or death

Example 3

The synergistic effect of various pretreatments with propiconazole on Chinmix is shown in Table 3. The investigation was carried out as described in Example 1.

TABLE 3

| Pretreatment* Propiconazole Dose (ng/fly) | Treatment Chinmix | Mortality (%) during 24 hours Alone | After pretreatment | Increase in effect (%) |
|---|---|---|---|---|
| 1000 | 1 | 10 | 55 | 45 |
| | 2 | 20 | 72.5 | 52.5 |
| | 4 | 55 | 100 | 52.5 |
| 500 | 1 | 10 | 45 | 35 |
| | 2 | 20 | 67.5 | 47.5 |
| | 4 | 55 | 100 | 45 |
| 100 | 1 | 10 | 45 | 35 |
| | 2 | 20 | 65 | 45 |
| | 4 | 55 | 100 | 45 |
| 50 | 1 | 10 | 35 | 25 |
| | 2 | 20 | 62.5 | 42.5 |
| | 4 | 55 | 100 | 45 |

*The pretreatments did not induce any symptom or death.

Example 4

The synergistic effect of treatments with various stereoisomers of propiconazole on Chinmix is shown in Table 4. The investigation was carried out as described in Example 1.

TABLE 4

| Pretreatment* with 100 ng of propiconazole | Effect of 3.4 ng of Chinmix mortality | Increase in effect (%) |
|---|---|---|
| — | 30 | — |
| Racemate | 65 | 35 |
| (2S,4R) | 82.5 | 52.5 |
| (2R,4S) | 60 | 30 |
| (2R,4R) | 77.5 | 47.5 |
| (2S,4S) | 82.5 | 52.5 |
| Piperonylbutoxide | 85 | 55 |

*The pretreatments did not induce any symptom or death.

Example 5

These investigations were carried out by using L4-grade larvae of moths (*Agrotis segetum*) collected from field in 4 parallel experiments and in 2 repetitions. The cultivating vessel of 2 liters volume was filled up to its half volume with earth. Subsequently 5 caterpillars were placed in each cultivating vessel. After a short rest period, while the larvae withdrew into the earth, barley plants treated with the compositions or combinations, respectively listed in Table 5 and then desiccated were put into the cultivating vessels.

The evaluation was started on the day following the treatment and then performed on the 2nd, 3rd and 4th days, too. In course of the evaluation, the dead larvae were counted. The effectiveness of the treatments was characterized by the percentage value of the deaths.

$$\text{Death \%} = \left(1 - \frac{x_1}{x_2}\right) \times 100$$

wherein $x_1$ means the number of (living) individuals after the treatment;

$x_2$ means the number of individuals before treatment.

The average values are shown in Table 5.

TABLE 5

| Treatment* | Dose (g/ha) | Mortality (%) 1st day | 2nd day | 3rd day | 4th day |
|---|---|---|---|---|---|
| Chinmix | 5 | 27.5 | 52.5 | 85.0 | 90.0 |
| Chinmix | 12.5 | 45.0 | 67.5 | 87.5 | 90.0 |
| Chinmix + dichlobutrazole | 5 + 125 | 65.0 | 100 | 100 | 100 |
| Chinmix + propiconazole | 12.5 + 125 | 72.5 | 100 | 100 | 100 |
| Chinmix + flutriafol | 12.5 + 125 | 70.0 | 100 | 100 | 100 |

TABLE 5-continued

| Treatment* | Dose (g/ha) | Mortality (%) | | | |
|---|---|---|---|---|---|
| | | 1st day | 2nd day | 3rd day | 4th day |
| Chinmix + triadimefon | 12.5 + 250 | 87.5 | 100 | 100 | 100 |

*No insecticidal effectiveness was shown by fungicidal treatments alone. In these examinations, the commercially available compositions Vigil (dichlobutrazole), Impact (flutriafol), Tilt (propiconazole), Bayleton (triadimefon), and Chinmix 5 EC (Chinmix) were used.

Example 6

The synergistic effect with Chinmix of several fungicides inhibiting the biosynthesis of ergosterol is shown on pyrethroid-resistant flies in Table 6. The Chinmix-resistance of the flies used in these examinations was developed in laboratory by means of selection pressure in such a way that 800 to 2000 flies of both sexes were topically treated with an $LD_{60}$-$LD_{90}$ dose of Chinmix in each generation and the surviving individuals were further propagated. Otherwise, the method described in Example 1 was followed.

TABLE 6

| Pretreatment with 500 ng* | Effect of 400 ng of chinmix mortality | Increase in effect mortality (%) |
|---|---|---|
| — | 65 | — |
| Propiconazole | 100 | >35 |
| Bitertanol | 100 | >35 |
| Fenarimol | 100 | >35 |

TABLE 6-continued

| Pretreatment with 500 ng* | Effect of 400 ng of chinmix mortality | Increase in effect mortality (%) |
|---|---|---|
| Flutriafol | 100 | >35 |
| Prochloraz | 100 | >35 |
| Etaconazole | 100 | >35 |
| Triadimefon | 100 | >35 |

*The pretreatments did not induce any symptom or death.

We claim:

1. A synergistic insecticidal composition which consists essentially of a synergistic mixture of:
   (a) Chinmix; and
   (b) propiconazole, in a synergistic weight ratio of 1:2 to 1:40.

2. A method of killing insects, which comprises the step of applying to a region to be protected, an insecticidally effective amount of a synergistic insecticidal composition which consists essentially of a synergistic mixture of:
   (a) Chinmix; and
   (b) propiconazole, in a synergistic weight ratio of 1:2 to 1:40.

* * * * *